(12) United States Patent
Hsiao

(10) Patent No.: US 8,262,277 B2
(45) Date of Patent: Sep. 11, 2012

(54) AROMA DIFFUSING NIGHT LAMP SYSTEM WITH AN ANGLE-ADJUSTABLE ELECTRIC PLUG

(76) Inventor: Ming Jen Hsiao, Toufen (TW)

(*) Notice: Subject to any disclaimer, the term of this patent is extended or adjusted under 35 U.S.C. 154(b) by 433 days.

(21) Appl. No.: 12/698,531

(22) Filed: Feb. 2, 2010

(65) Prior Publication Data

US 2011/0110118 A1 May 12, 2011

Related U.S. Application Data

(63) Continuation-in-part of application No. 12/616,560, filed on Nov. 11, 2009, now abandoned.

(51) Int. Cl.
*F21V 33/00* (2006.01)
(52) U.S. Cl. ......... 362/643; 392/392; 392/386; 392/391
(58) Field of Classification Search ................. 362/643, 362/96; 392/392, 386, 391, 394, 359
See application file for complete search history.

(56) References Cited

U.S. PATENT DOCUMENTS

| | | | | |
|---|---|---|---|---|
| 3,248,530 A * | 4/1966 | Titmas | ............ | 362/643 |
| 3,443,083 A * | 5/1969 | Curran | ............ | 362/643 |
| 3,948,445 A * | 4/1976 | Andeweg | ............ | 239/53 |
| 4,346,059 A * | 8/1982 | Spector | ............ | 422/125 |
| 7,350,720 B2 * | 4/2008 | Jaworski et al. | ............ | 239/55 |
| 2004/0257798 A1 * | 12/2004 | Hart et al. | ............ | 362/96 |

* cited by examiner

*Primary Examiner* — Laura Tso
(74) *Attorney, Agent, or Firm* — Chun-Ming Shih

(57) ABSTRACT

An aroma diffusing night lamp system having the characteristics of high heating performance, high level of safety and angle adjustability is disclosed to include a night lamp unit formed of a lamp socket holding a light emitting device, an electric plug rotatably coupled to the lamp socket and a safety lampshade surrounding the light emitting device, and an aroma diffuser unit formed of an electrically insulative heater holder, a heater carried in the electrically insulative heater holder and an outer lampshade that is mounted on the lamp socket around the safety lampshade and defines a top trough that holds an aromatic substance and has the bottom wall thereof kept in contact with the heater for enabling the aromatic substance to be heated into vapor safely.

10 Claims, 9 Drawing Sheets

AROMA DIFFUSING NIGHT LAMP SYSTEM WITH AN ANGLE-ADJUSTABLE ELECTRIC PLUG

CROSS-REFERENCE TO RELATED APPLICATION

This invention is a continuation-in-part of U.S. patent application Ser. No. 12/616,560, entitled "Aroma diffusing night lamp system", filed on Nov. 11, 2009 now abandoned.

BACKGROUND OF THE INVENTION

1. Field of the Invention

The present invention relates to scent releasing devices and more specifically, to an aroma diffusing night lamp system that combines a night lamp unit and an aroma diffuser unit together and that uses an angle-adjustable electric plug to obtain the necessary working power supply.

2. Description of the Related Art

Conventional night lamp does not allow adjustment of the angular position of the two parallel metal prongs of their electric plugs to fit different indoor installation requirements.

There are night lamps with an added aroma diffusing function. These night lamps combine an angle-adjustable night lamp unit and an aroma diffuser unit. When the night lamp unit of a night lamp is connected to a city power supply outlet, the radiating heat from the night lamp unit heats an aromatic substance, for example, essential oil in the aroma diffuser unit into vapor, providing a romantic atmosphere and enhancing the value of use of the night lamp.

Although conventional aroma diffusing night lamps allow adjustment of the installation angle of the night lamp unit, their angle-adjustable structure wear quickly with use or is difficult to adjust to the accurate angle. After installation, the applied essential oil may fall from the lampshade accidentally.

Further, regular aroma diffusing night lamps commonly use an incandescent lamp bulb to emit light and to heat the supplied aromatic substance. The heating efficiency of an incandescent lamp is low. Further, the aroma diffuser unit of a regular aroma diffusing night lamp is less stable. In consequence, a gap may be produced in the electric conducting structure, affecting the performance of electric conductivity. Further, regular aroma diffusing night lamps have no means to seal the electric conducting component parts. If the aromatic fluid leaks out, a short circuit accident may occur.

Further, the angle adjustment structures of conventional angle adjustable aroma diffusing nigh lamps are commonly not very stable. After adjustment of the desired angle, the aroma diffuser unit may be biased relative to the night lamp unit accidentally.

Further, some known aroma diffusing nigh lamps use a lampshade prepared from a light-transmissive heat-resisting hard material such as ceramic or glass. During installation, small retaining and/or fastening members are used to affix the lampshade in place. The use of these retaining and/or fastening members may cause the lampshade to break, shortening the night lamp lifespan and threatening user safety.

SUMMARY OF THE INVENTION

The present invention has been accomplished to provide an aroma diffusing night lamp system with an angle-adjustable electric plug, which eliminates the drawbacks of the aforesaid prior art designs.

To achieve this and other objects of the present invention, an aroma diffusing night lamp system comprises a night lamp unit and an aroma diffuser unit. The night lamp unit comprises a lamp socket, a light emitting device mounted in the lamp socket, an electric plug coupled and rotatable relative to the lamp socket and adapted for electrically connecting the lamp socket to an external city power supply outlet, and a safety lampshade surrounding the light emitting device. The aroma diffuser unit comprises an electrically insulative heater holder mounted in the safety lampshade of the night lamp unit, a heater carried in thee electrically insulative heater holder and electrically connected to the electric socket of the night lamp unit by power wires and an outer lampshade mounted on the lamp socket and surrounding the safety lampshade. The outer lampshade defines a top trough for holding an aromatic substance. The top tough has the bottom wall thereof kept in contact with the heater and adapted for transferring heat energy from the heater to the aromatic substance carried in the top trough to heat the aromatic substance into vapor.

In one embodiment of the present invention, the light emitting device comprises at least one light emitting diode.

In one embodiment of the present invention, the heater is a cement resistor.

Further, the electric plug comprises an electric plug body having a cylindrical rear side, a gear wheel fixedly located on the cylindrical rear side of the electric plug body, a first gear wheel cover and a second gear wheel cover. The first gear wheel cover has two arched arms and an arched groove defined by the two arched arms thereof. The second gear wheel cover has two arched arms and an arched groove defined by the two arched arms thereof. The arched arms of the first gear wheel cover are respectively abutted against the arched arms of the second gear wheel cover around the cylindrical rear side of the electric plug body to keep the arched grooves of the first gear wheel cover and the second gear wheel cover in friction engagement with the gear wheel.

Further, the lamp socket comprises two socket shells fastened together and a damping spring leaf mounted in one socket shell for securing the gear wheel of the electric plug. One socket shell has a round hole for receiving a part of the gear wheel of the electric plug, and a locating groove formed in the round hole for receiving the damping spring leaf. The damping spring leaf is positioned in the locating groove and stopped against a part of the gear wheel of the electric plug. Further, the damping spring leaf has a W-shaped configuration and a protruding damping portion located on the middle part thereof. The locating groove in the round hole of one socket shell is configured to fit the W-shaped configuration of the damping spring leaf.

The aroma diffuser unit further comprises a first top cover, a second top cover and at least one elastic member. The first top cover has at least one vertically extending groove. The second top cover has at least one vertically extending groove. The first top cover and the second top cover are abutted together such that each vertically extending groove of the first top cover is coupled to one respective vertically extending groove of the second top cover to form one vertical through hole. The first top cover and the second top cover are mounted in between the safety lampshade of the night lamp unit and the electrically insulative heater holder of the aroma diffuser. The at least one elastic member is respectively inserted into the at least one vertical through hole in between the first top cover and the second top cover. The electrically insulative heater holder has at least one foot member extended from the bottom side thereof and inserted into the at least one vertical through holes in between the first top cover and the second top cover and supported on the at least one elastic member.

The night lamp unit further comprises a retainer mounted on the electric socket to secure the outer lampshade to the electric socket. The retainer has a bottom ring mounted on the top side of the electric socket and a plurality of retaining pawls upwardly extended from the bottom ring and equiangularly spaced from one another for securing the outer lampshade.

Further, each retaining pawl of the retainer has a hooked portion, a top slope located on the top side of the hooked portion and a recessed portion located on the bottom side of the hooked portion.

Further, the electric plug has a plurality of triangular retaining blocks equiangularly spaced around the cylindrical rear side thereof. The gear wheel is a gear ring, having a plurality of triangular retaining grooves equiangularly arranged on the inner diameter thereof and respectively forced into engagement with the triangular retaining blocks of the electric plug.

Thus, subject to the use of the cement resistor for heating the supplied aromatic substance into vapor directly, the invention achieves an excellent heating effect. Further, subject to the arrangement between the gear wheel and damping spring leaf, the adjustment of the angular position of the electric plug relative to the lamp socket is easy and accurate, avoiding damage. Further, subject to the use of the safety lampshade to enclose the light emitting device and the power wires, the invention assures a high level of safety.

DETAILED DESCRIPTION OF THE PREFERRED EMBODIMENT

Figure 1:
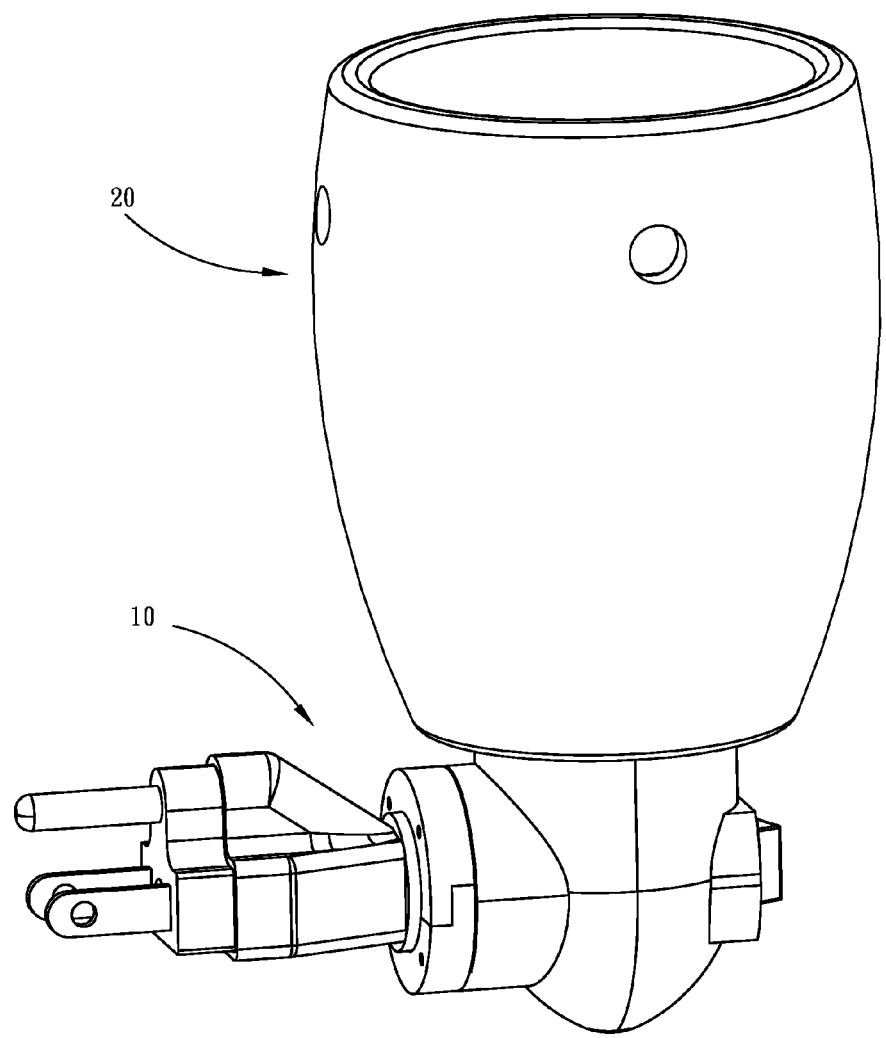
FIG. 1 is an elevational view of an aroma diffusing night lamp system in accordance with the present invention.

Referring to FIG. 1, an aroma diffusing night lamp system with an angle-adjustable electric plug in accordance with the present invention is shown comprising a night lamp unit 10 and an aroma diffuser unit 20.

Figure 2:
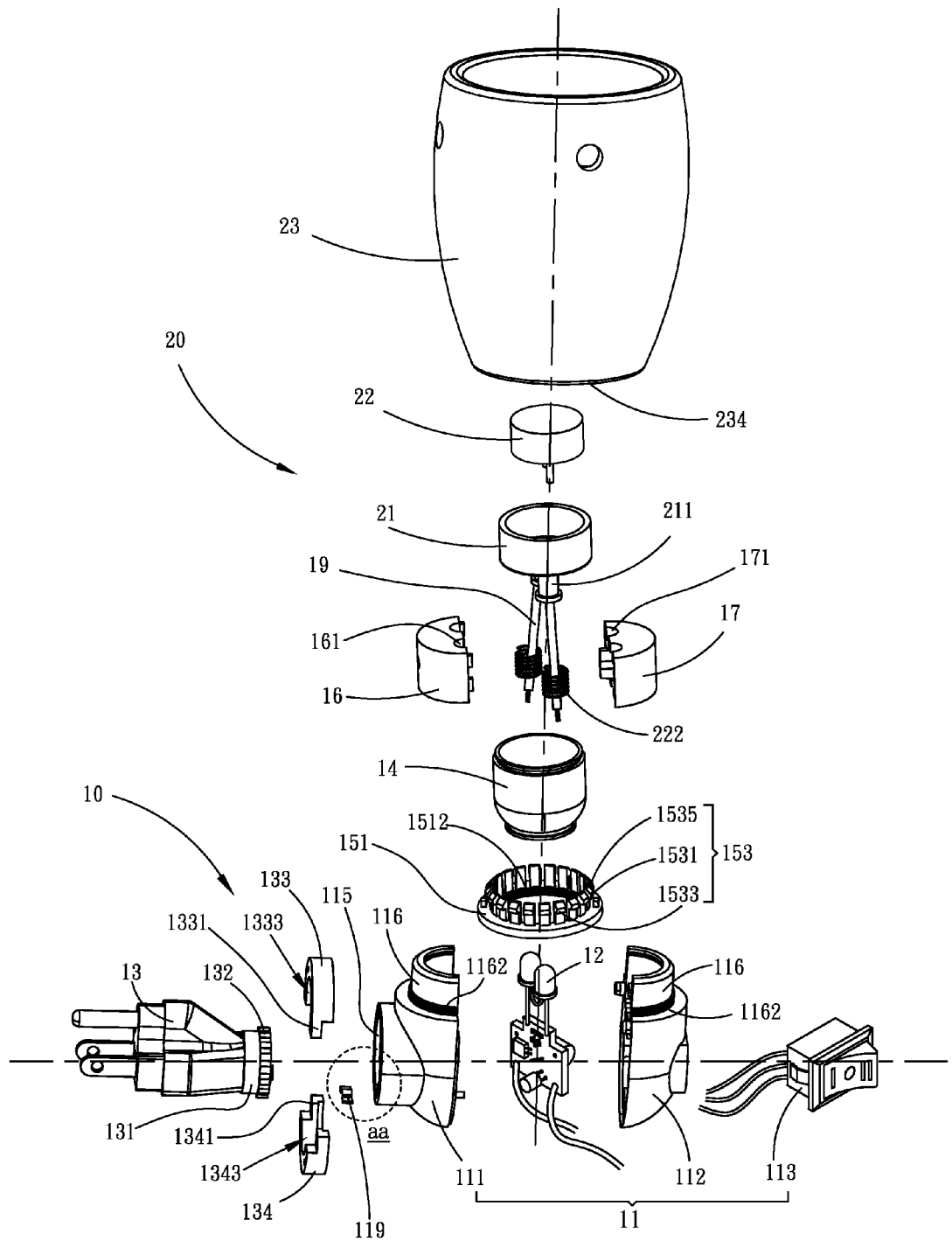
FIG. 2 is an exploded view of the aroma diffusing night lamp system in accordance with the present invention.
Figure 3:
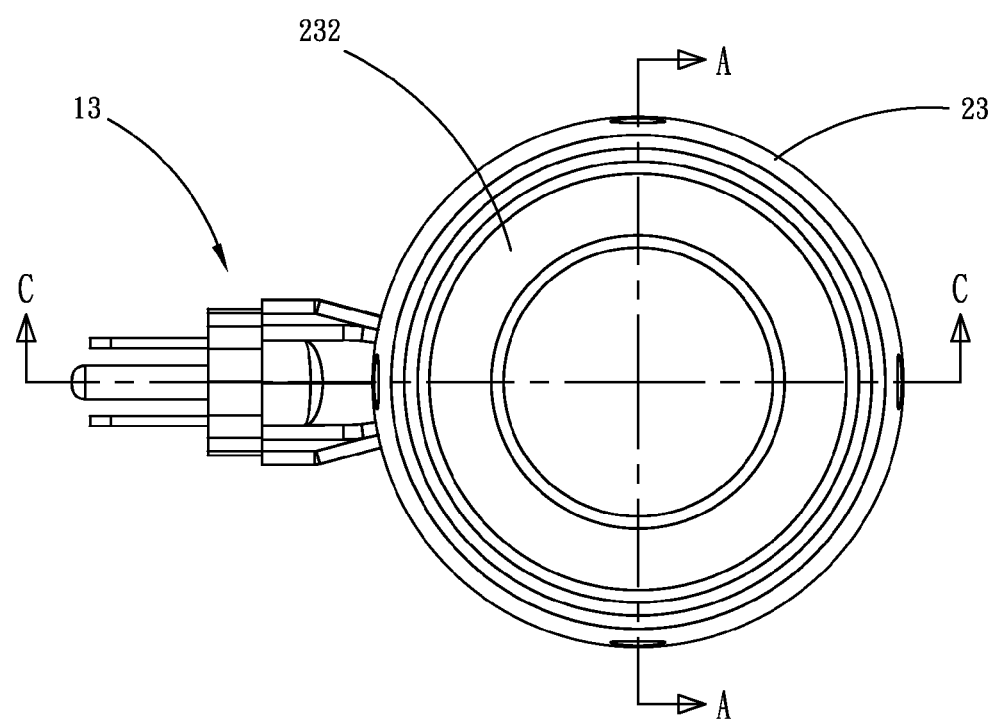
FIG. 3 is a schematic top view of the aroma diffusing night lamp system in accordance with the present invention.
Figure 4:
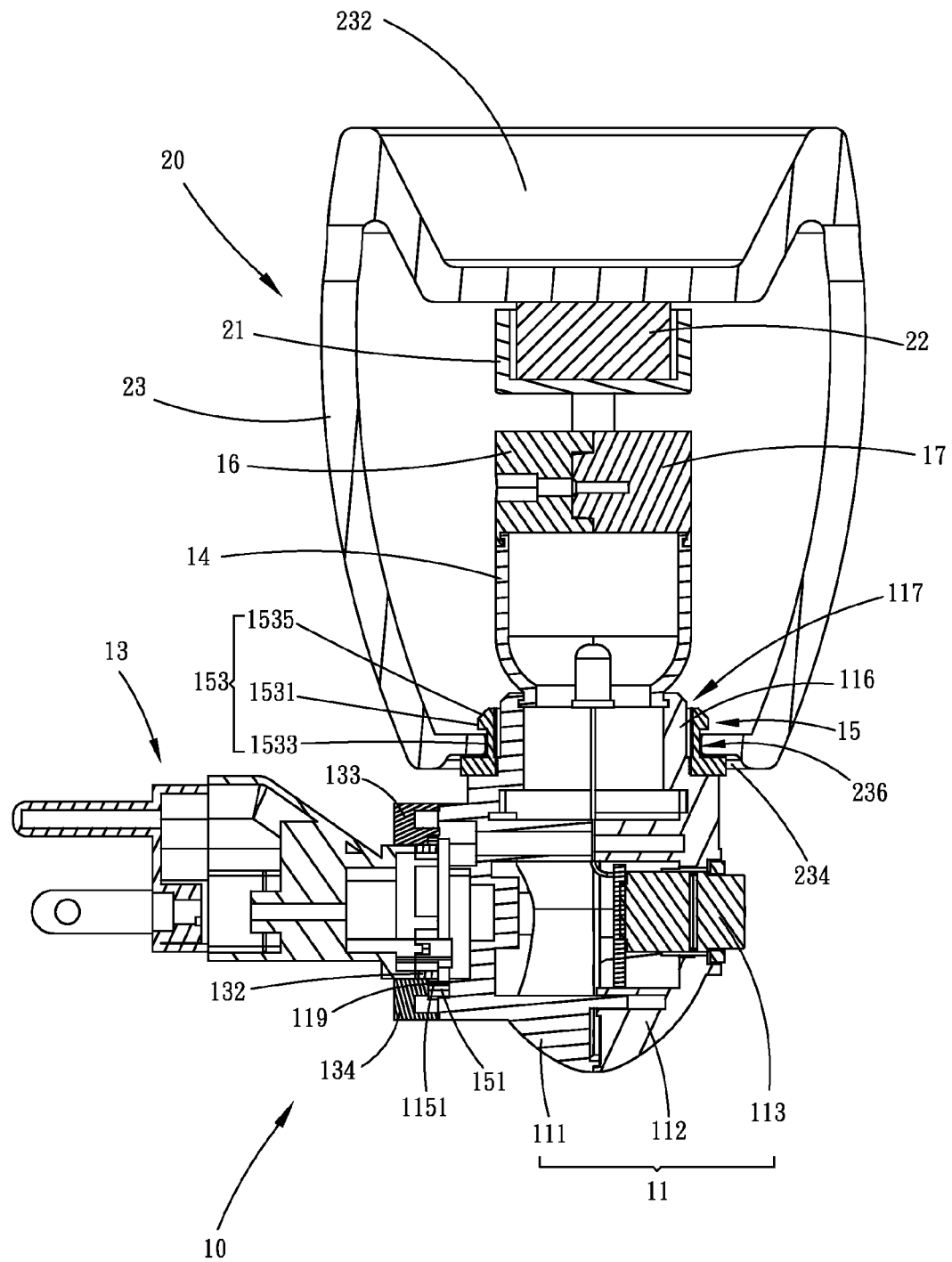
FIG. 4 is a sectional view taken along line A-A of FIG. 3.

Referring to FIGS. 2~4, the night lamp unit 10 comprises a lamp socket 11, a light emitting device 12, an electric plug 13 and a safety lampshade 14. The light emitting device 12 is mounted in the lamp socket 11 and adapted to emit light through the safety lampshade 14. The safety lampshade 14 surrounds the light emitting device 12. The electric plug 13 is pivotally coupled to the lamp socket 11 and angularly adjustable relative to the lamp socket 11.

Further, the electric plug 13 comprises an electric plug body 131, a gear wheel 232 located on the cylindrical rear side of the electric plug body 131, a first gear wheel cover 133 and a second gear wheel cover 134. The first gear wheel cover 133 has two arched arms 1331, defining an arched groove 1332.

The second gear wheel cover 134 has two arched arms 1341, defining an arched groove 1342. The arched arms 1331 of the first gear wheel cover 133 are respectively abutted against the arched arms 1341 of the second gear wheel cover 134 around the cylindrical rear side of the electric plug body 131 to keep the arched grooves 1332 and 1342 in friction engagement with the gear wheel 132. Thus, the gear wheel 231 can be rotated with the electric plug body 131 relative to the first gear wheel cover 133 and the second gear wheel cover 134. After rotation, the friction force between the gear wheel 231 and the first and second gear wheel covers 133 and 134 secures the gear wheel 132 and the electric plug body 131 to the first and second gear wheel covers 133 and 134 firmly in position.

The lamp socket 11 of the night lamp unit 10 comprises two symmetrical socket shells 111 and 112 and a power switch 113. The safety lampshade 14 is fastened to the two symmetrical socket shells 111 and 112 at the top side. The two symmetrical socket shells 111 and 112 surround the light emitting device 12, holding the light emitting device 12 firmly in position. The aroma diffusing night lamp keeps the light emitting device 12 and the power wires 19 and other connected electric components on the inside of the safety lampshade 14, avoiding breaking of the outer lampshade and any possible accidental electric leakage due to accidental leakage of the applied aromatic substance or essential oil. The power switch 113 is installed in one socket shell 112 and exposed to the outside. After connection of the electric plug 13 to an external power source and pressing of the power switch 113, the lamp socket 11 and light emitting device 12 of the night lamp unit 10 and the aroma diffuser unit 20 are electrically connected to emit light and to produce heat. On the contrary, when the user presses the power switch 113 again, the lamp socket 11 and light emitting device 12 of the night lamp unit 10 are electrically disconnected. The socket shell 111 has a round hole 115 for accommodating a part of the gear wheel 132 of the electric plug 13.

Figure 5:
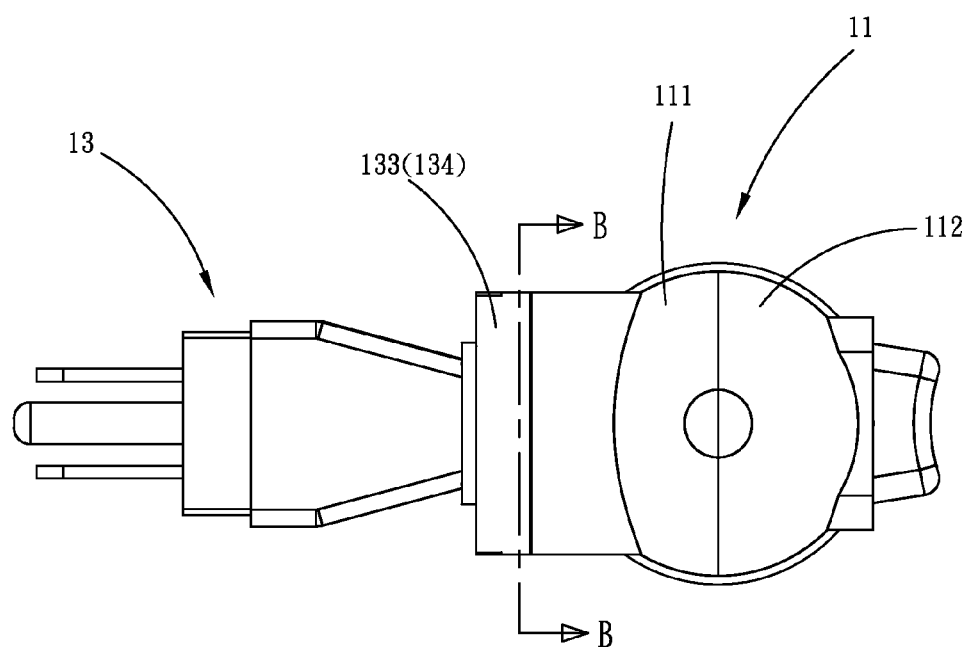
FIG. 5 is a schematic bottom view of the aroma diffusing night lamp system in accordance with the present invention.
Figure 6:
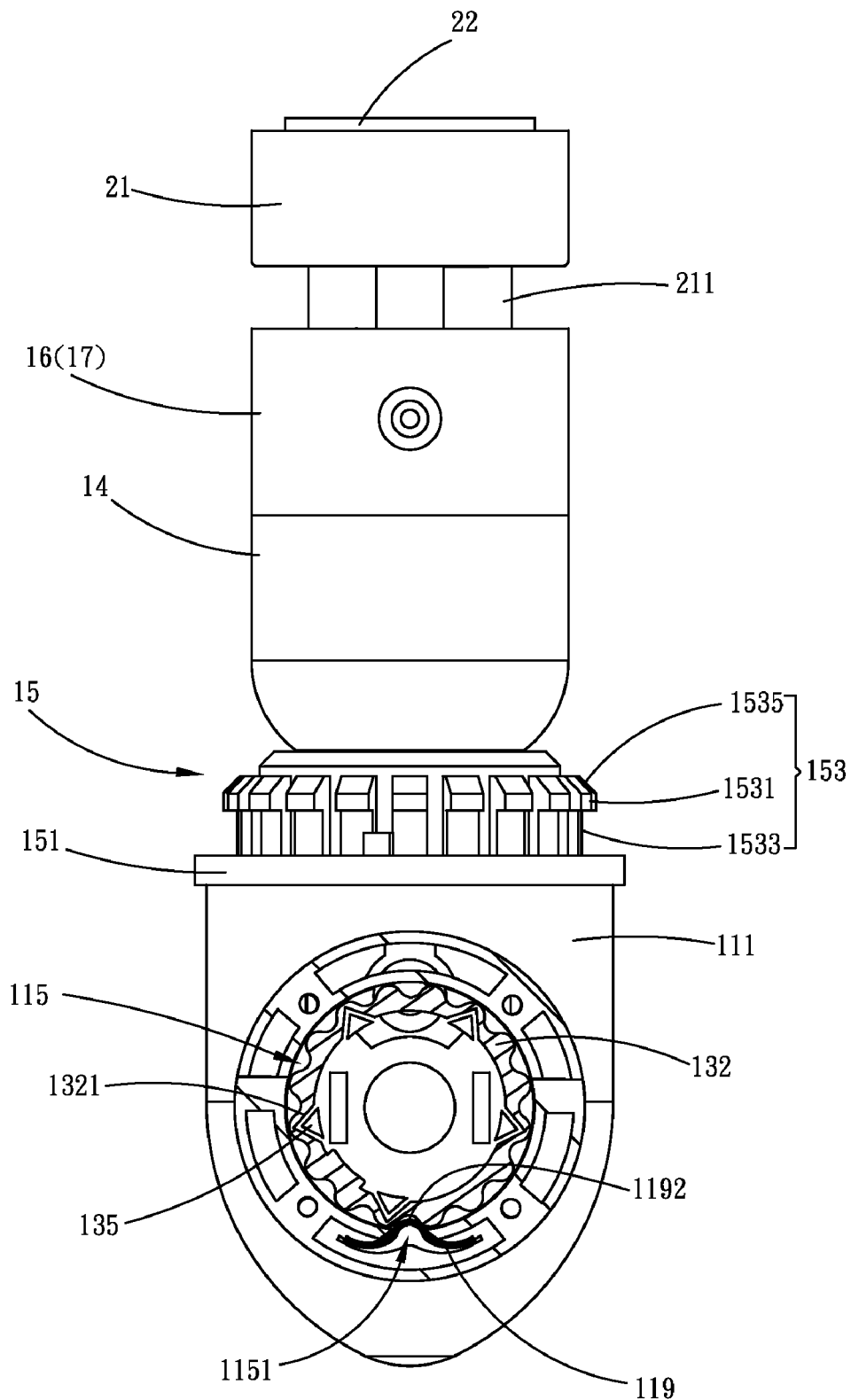
FIG. 6 is a sectional view taken along line B-B of FIG. 5.
Figure 7:
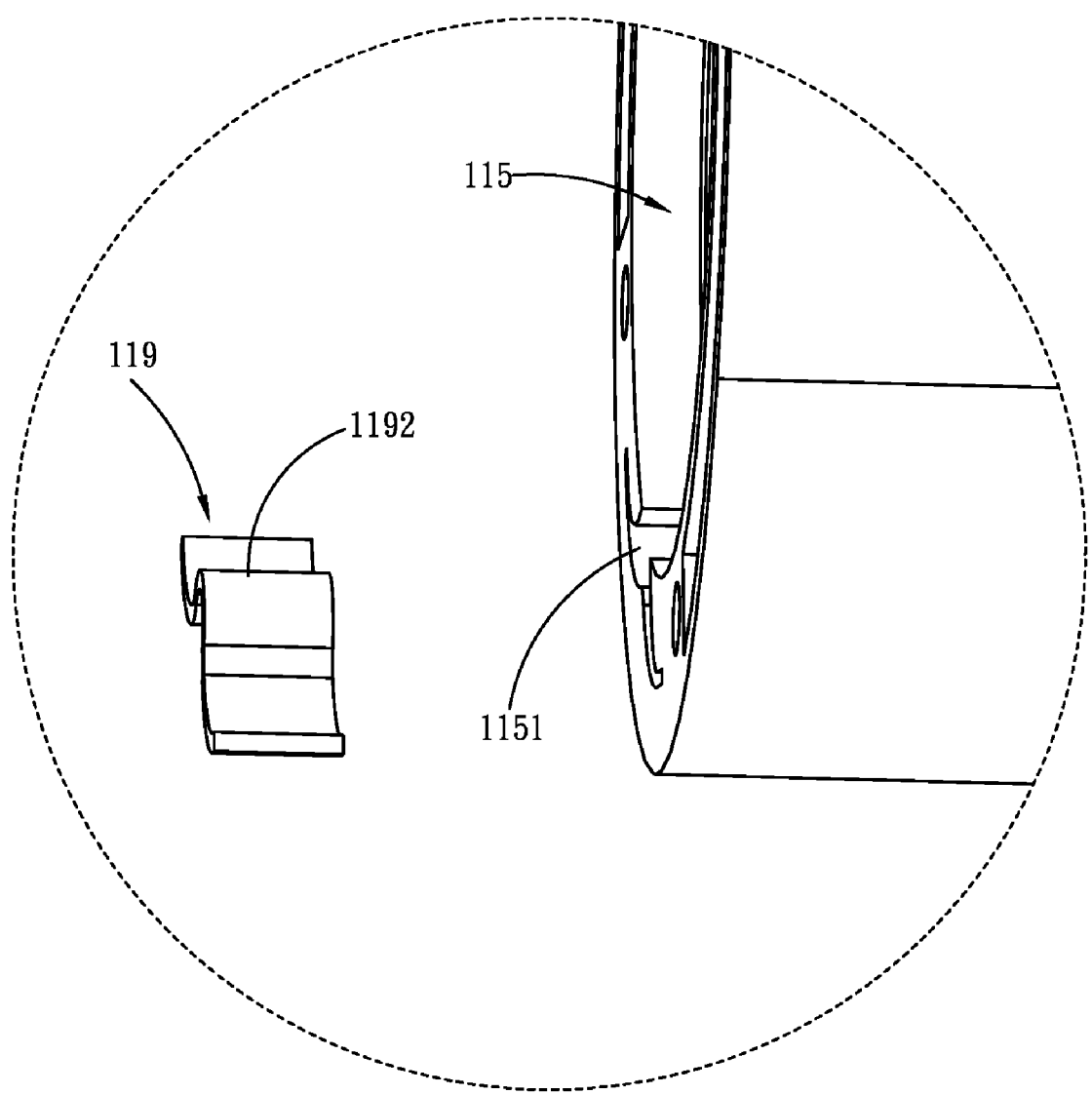
FIG. 7 is an enlarged view of part aa of FIG. 2.

Referring to FIGS. 5~7, the lamp socket 11 further comprises a damping spring leaf 119 having, for example, a W-shaped configuration. The damping spring leaf 119 has a protruding damping portion 1192 on the middle. The socket shell 111 has a locating groove 1151 in the round hole 115 configured to fit the W-shaped configuration of the damping spring leaf 119. After mounting of the damping spring leaf 119 in the locating groove 1151 inside the round hole 115, the protruding damping portion 1192 of the damping spring leaf 119 is kept suspending in the round hole 115. When the gear wheel 132 of the electric plug 13 is partially inserted into the round hole 115 of the socket shell 111, the protruding damping portion 1192 of the damping spring leaf 119 is stopped against the toothed periphery of the gear wheel 132, holding the gear wheel 132 in place and allowing rotation of the gear wheel 132 with the electric plug body 131 relative to the lamp socket 11 to adjust the angle of the electric plug 13. Thus, the user can adjust the angle of the electric plug 13 relative to the electric socket 11 accurately.

Figure 8:
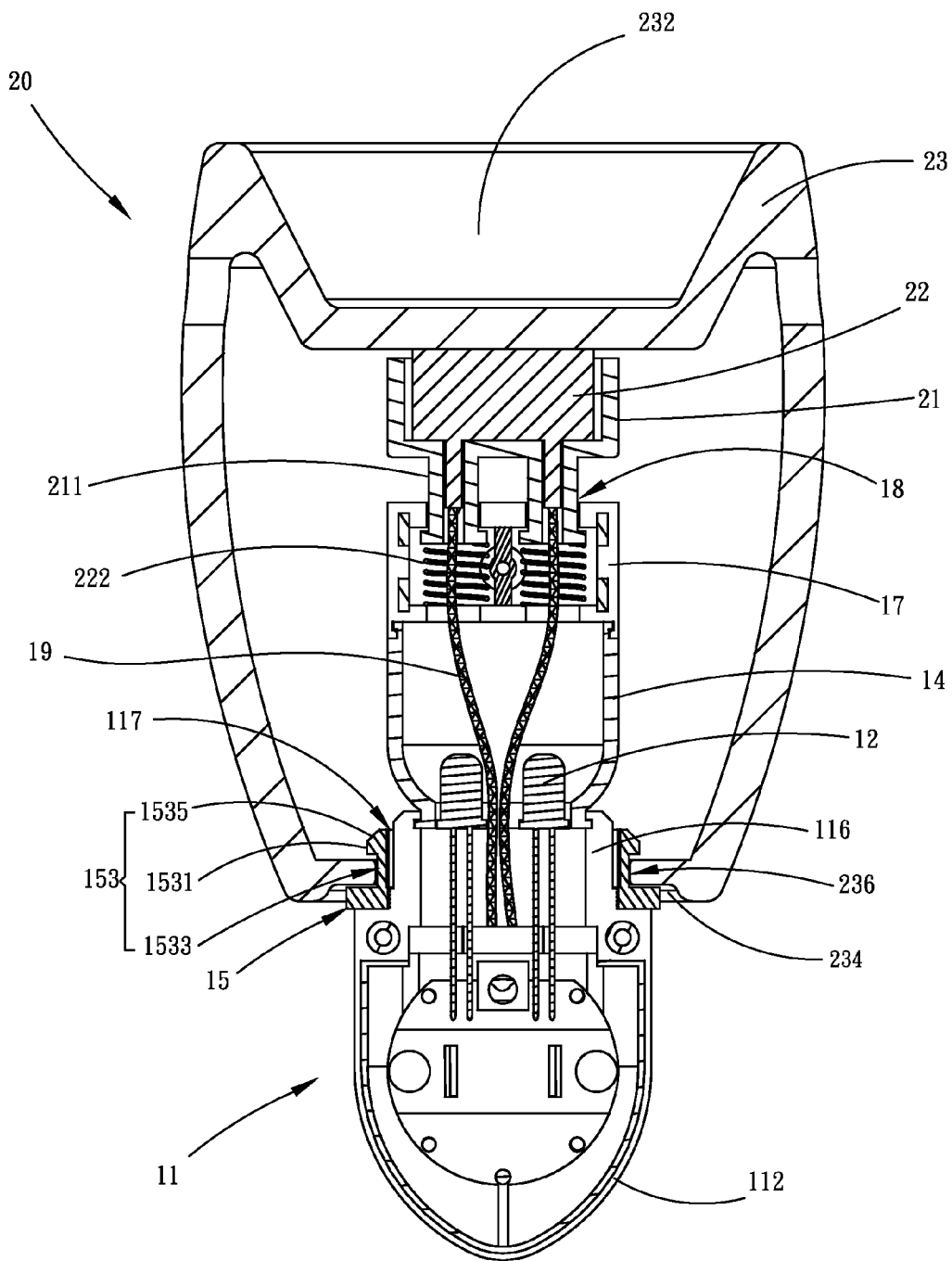
FIG. 8 is a sectional view taken along line C-C of FIG. 3.

Referring to FIG. 8 and FIG. 2 again, the aroma diffuser unit 20 comprises an electrically insulative heater holder 21, a heater 22 and an outer lampshade 23. The heater 21 according to the present preferred embodiment is a cement resistor. Further, the electrically insulative heater holder 21 according to the present preferred embodiment is made from a phenol-formaldehyde plastic material (bakelite). The electrically insulative heater holder 21 is capped on the safety lampshade 14 of the night lamp unit 10. The outer lampshade 23 has its bottom side kept in contact with the heater 22. The heater 22 is carried in the electrically insulative heater holder 21 and electrically connected to the electric plug 13 by the power wires 19 for heating the outer lampshade 23.

According to the present preferred embodiment, the outer lampshade 23 of the aroma diffuser unit 20 has a shadow fluid trough 232 defined in the top side thereof, a bottom edge 234 located on the bottom side thereof and a through hole 236 cut through the center of the bottom edge 234. The outer lampshade 23 is prepared from a light transmissive material. The through hole 236 on the bottom edge 234 of the outer lampshade 23 is coupled to the lamp socket 11 of the night lamp unit 10 around the safety lampshade 14. The bottom wall of the shadow fluid trough 232 is kept in contact with the top wall of the heater 22. An aromatic substance (such as essential oil, fragrant wax or the like) is put in the shadow fluid trough 232. Thus, by means of using cement resistors as heat source means to heat the applied aromatic fluid instead of an incandescent lamp bulb, the invention provides a stable heating effect. According to the present preferred embodiment, the light emitting device 12 of the night lamp unit 10 uses LEDs (light emitting diodes) to emit light, meeting modern green safety codes.

The aroma diffuser unit 10 further comprises a first top cover 16, a second top cover 17 and at least one, for example, two elastic members 222. The elastic members 222 can be compression springs or rubber blocks. According to this embodiment, the elastic members 222 are compression springs. The first top cover 16 has a plurality of vertically extending grooves 161. The second top cover 17 has a plurality of vertically extending grooves 171. The first top cover 16 and the second top cover 17 are abutted together. Thus, vertically extending grooves 161 of the first top cover 16 are respectively coupled to the vertically extending grooves 171 of the second top cover 17, forming vertical through holes 18. The first top cover 16 and the second top cover 17 are mounted in between the safety lampshade 14 of the night lamp unit 10 and the electrically insulative heater holder 21 of the aroma diffuser 20. The electrically insulative heater holder 21 has at least one, for example, two foot members 211 extended from the bottom side thereof. The spring members 222 are respectively inserted into the vertical through holes 18. The foot members 211 of the electrically insulative heater holder 21 are respectively inserted into the vertical through holes 18 and supported on the spring members 222. The spring members 222 impart an upward spring force to the electrically insulative heater holder 21, thereby forcing the heater 22 against the bottom wall of the shadow fluid trough 232 of the outer lampshade 23. Therefore, the heater 22 is constantly and stably kept in close contact with the bottom wall of the shadow fluid trough 232 of the outer lampshade 23.

The night lamp unit 10 further comprises a retainer 15. The retainer 15 has a bottom ring 151 and a plurality of retaining pawls 153. The retainer 15 is mounted on the top side of the lamp socket 11 to secure the outer lampshade 23. Each retaining pawl 153 has a hooked portion 1531 and a recessed portion 1533. The hooked portion 1531 has a top slope 1535. The bottom ring 151 defines therein an inner thread 1512. Each of the socket shells 111 and 112 has an externally threaded top flange 116. The inner thread 1512 of the retainer 15 is threaded onto the externally threaded top flanges 116 of the socket shells 111 and 112 of the lamp socket 11 such that an annular space 117 is defined between the externally threaded top flanges 116 of the socket shells 111 and 112 of the lamp socket 11 and the retaining pawls 153.

When coupling the through hole 236 on the bottom edge 234 of the outer lampshade 23 to the lamp socket 11 of the night lamp unit 10 around the safety lampshade 14, the periphery of the through hole 236 will be moved downwardly over the top slopes 1535 of the retaining pawls 153 of the retainer 15 to force retaining pawls 153 into the annular space 117 toward the externally threaded top flanges 116 of the socket shells 111 and 112 of the lamp socket 11 so that the through hole 236 on the bottom edge 234 of the outer lampshade 23 an be forced into engagement with the recessed portions 1533 of the retaining pawls 153. The retaining pawls 153 are equiangularly arranged on the top side of the bottom ring 151 for evenly distributing the contact pressure when the bottom edge 234 of the ceramic or glass outer lampshade 23 is attached to the retainer 15 at the top side of the lamp socket 11, avoiding concentration of shear stress or flexural shear stress on contact points between the outer lampshade 23 and the retainer 15.

The aroma diffusing night lamp system with an angle-adjustable electric plug uses the safety lampshade 14 to shield the light emitting device 12, the power wires 19 and other connected electric components, avoiding breaking of the outer lampshade 23 and any possible accidental electric leakage due to accidental leakage of the applied aromatic substance or essential oil.

Figure 9:
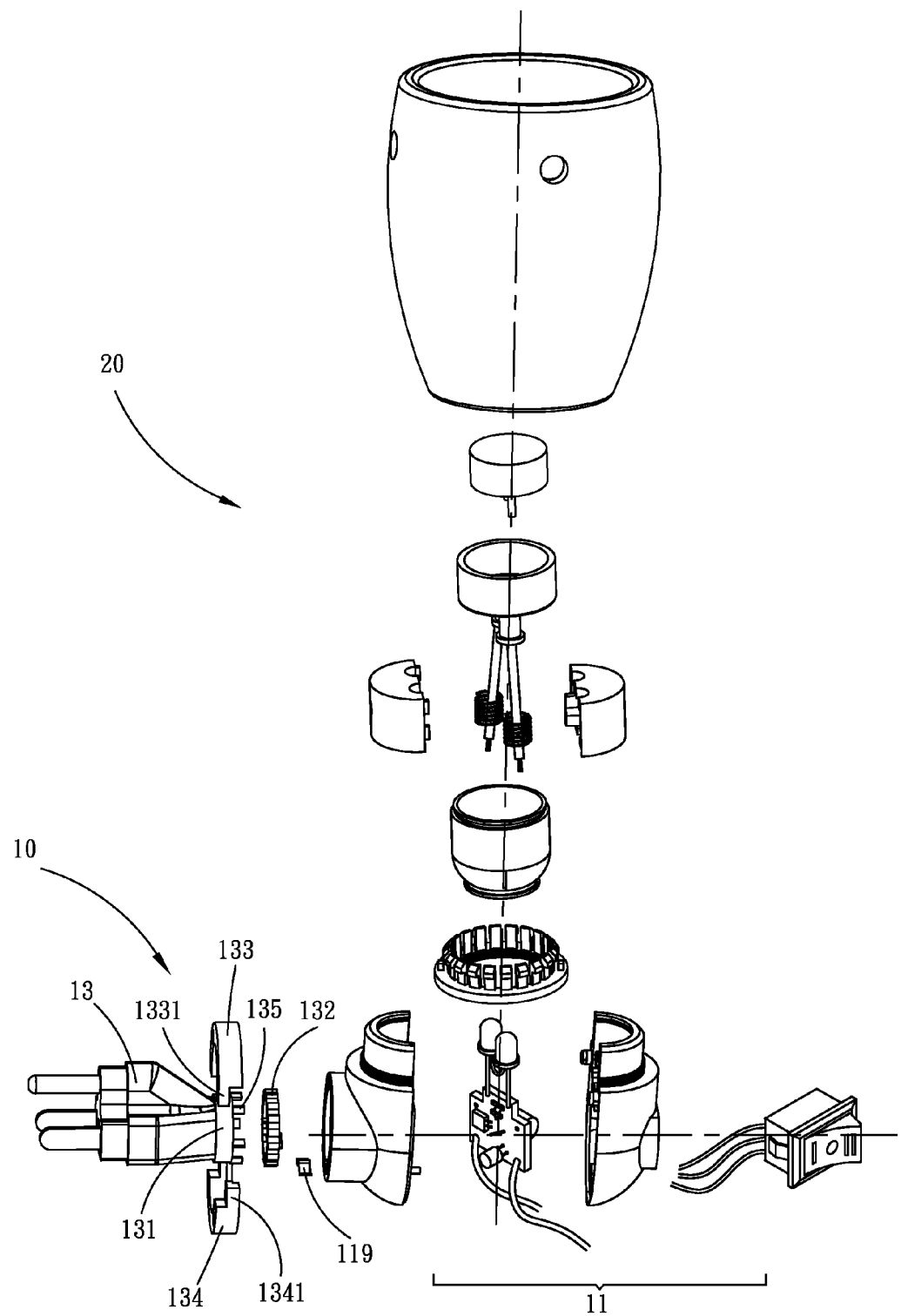
FIG. 9 is an exploded view of an alternate form of the aroma diffusing night lamp system in accordance with the present invention.

FIG. 9 shows an alternate form of the present invention. According to this alternate form, the cylindrical rear side of the electric plug body 131 of the electric plug 13 has a plurality of triangular retaining blocks 135 equiangularly spaced around the cylindrical rear side thereof. The gear wheel 135 is a gear ring, having a plurality of triangular retaining grooves 1321 equiangularly arranged on the inner diameter thereof and respectively forced into engagement with the triangular retaining blocks 135 of the electric plug body 131 of the electric plug 13. After installation of the gear wheel 135 in the cylindrical rear side of the electric plug body 131 of the electric plug 13, the electric plug 13 can then be fastened with the gear wheel covers 133 and 134 to the lamp socket 11 and then rotated relative to the lamp socket 11 to the desired angle.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. An aroma diffusing night lamp system, comprising:
   a night lamp unit, said night lamp unit comprising a lamp socket, a light emitting device mounted in said lamp socket, an electric plug coupled and rotatable relative to said lamp socket and adapted for electrically connecting said lamp socket to an external city power supply outlet, and a safety lampshade surrounding said light emitting device; and
   an aroma diffuser unit, said aroma diffuser unit comprising an electrically insulative heater holder mounted in said safety lampshade of said night lamp unit, a heater carried in said electrically insulative heater holder and electrically connected to said electric socket of said night lamp unit by power wires and an outer lampshade mounted on said lamp socket and surrounding said safety lampshade, said outer lampshade defining a top trough for holding an aromatic substance, said outer lampshade being kept in contact with said heater and adapted for transferring heat energy from said heater to the aromatic substance carried in said top trough to heat the aromatic substance into vapor.

2. The aroma diffusing night lamp system as claimed in claim 1, wherein said light emitting device comprises at least one light emitting diode.

3. The aroma diffusing night lamp system as claimed in claim 1, wherein said heater is a cement resistor.

4. The aroma diffusing night lamp system as claimed in claim 1, wherein said electric plug comprises an electric plug body having a cylindrical rear side, a gear wheel fixedly located on the cylindrical rear side of said electric plug body, a first gear wheel cover and a second gear wheel cover, said first gear wheel cover having two arched arms and an arched groove defined by the two arched arms thereof, said second gear wheel cover having two arched arms and an arched groove defined by the two arched arms thereof, the arched arms of said first gear wheel cover being respectively abutted against the arched arms of said second gear wheel cover around the cylindrical rear side of said electric plug body to keep the arched grooves of said first gear wheel cover and said second gear wheel cover in friction engagement with said gear wheel.

5. The aroma diffusing night lamp system as claimed in claim 4, wherein said lamp socket comprises two socket shells fastened together and a damping spring leaf mounted in one said socket shell for securing said gear wheel of said electric plug, one said socket shell having a round hole for receiving a part of said gear wheel of said electric plug and a locating groove formed in said round hole for receiving said damping spring leaf, said damping spring leaf being positioned in said locating groove and stopped against a part of said gear wheel of said electric plug.

6. The aroma diffusing night lamp system as claimed in claim 5, wherein said damping spring leaf has a W-shaped configuration and a protruding damping portion located on a middle part thereof; said locating groove in said round hole is configured to fit the W-shaped configuration of said damping spring leaf.

7. The aroma diffusing night lamp system as claimed in claim 5, wherein said aroma diffuser unit further comprises a first top cover, a second top cover and at least one elastic member, said first top cover having at least one vertically extending groove, said second top cover having at least one vertically extending groove, said first top cover and said second top cover being abutted together such that each vertically extending groove of said first top cover is coupled to one respective vertically extending groove of said second top cover to form one vertical through hole, said first top cover and said second top cover being mounted in between said safety lampshade of said night lamp unit and said electrically insulative heater holder of said aroma diffuser, said at least one elastic member being respectively inserted into the at least one vertical through hole in between said first top cover and said second top cover; said electrically insulative heater holder has at least one foot member extended from a bottom side thereof and inserted into the at least one vertical through holes in between said first top cover and said second top cover and supported on said at least one elastic member.

8. The aroma diffusing night lamp system as claimed in claim 1, wherein said night lamp unit further comprises a retainer mounted on said electric socket to secure said outer lampshade to said electric socket, said retainer having a bottom ring mounted on a top side of said electric socket and a plurality of retaining pawls upwardly extended from said bottom ring and equiangularly spaced from one another for securing said outer lampshade.

9. The aroma diffusing night lamp system as claimed in claim 8, wherein each said retaining pawl has a hooked portion, a top slope located on a top side of said hooked portion and a recessed portion located on a bottom side of said hooked portion.

10. The aroma diffusing night lamp system as claimed in claim 4, wherein said electric plug has a plurality of triangular retaining blocks equiangularly spaced around a cylindrical rear side thereof; said gear wheel is a gear ring, having a plurality of triangular retaining grooves equiangularly arranged on the inner diameter thereof and respectively forced into engagement with the triangular retaining blocks of said electric plug.

* * * * *